United States Patent [19]

Schmidt et al.

[11] 4,309,538
[45] Jan. 5, 1982

[54] PREPARATION OF 4-AMINO-6-TERT.-BUTYL-3-ALKYLTHIO-1,2,4-TRIAZIN-5(4H)-ONES

[75] Inventors: Thomas Schmidt, Haan; Andreas Wittig, Wuppertal; Hans-Peter Sehnem, Wuppertal; Hans Krätzer, Wuppertal; Rolf-Jürgen Singer, Wuppertal, all of Fed. Rep. of Germany

[73] Assignee: Bayer Aktiengesellschaft, Leverkusen, Fed. Rep. of Germany

[21] Appl. No.: 227,442

[22] Filed: Jan. 22, 1981

[30] Foreign Application Priority Data

Jan. 31, 1980 [DE] Fed. Rep. of Germany ....... 3003541
Jan. 31, 1981 [DE] Fed. Rep. of Germany ....... 3003542

[51] Int. Cl.³ .......................................... C07D 253/06
[52] U.S. Cl. .................................................. 544/182
[58] Field of Search ....................................... 544/182

[56] References Cited

U.S. PATENT DOCUMENTS 4,175,188 11/1979 Klenk et al. ........................ 544/182

Primary Examiner—John M. Ford
Attorney, Agent, or Firm—Sprung, Felfe, Horn, Lynch & Kramer

[57] ABSTRACT

In the preparation of 4-amino-6-tert.-butyl-3-alkylthio-1,2,4-triazin-5(4H)-ones of the formula

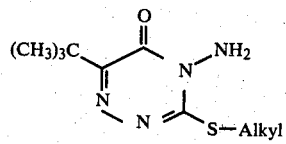

wherein (a) pivaloyl cyanide of the formula

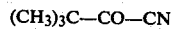

is converted to a derivative of trimethylpyruvic acid, (b) the derivative is condensed with thiocarbohydrazide of the formula

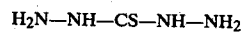

to form 4-amino-6-tert.-butyl-3-mercapto-1,2,4-triazin-5(4H)-one, and (c) that is alkylated to form the indicated end products, the improvement which comprises effecting (a) by reacting the pivaloyl cyanide with a strong anhydrous inorganic acid at about −50° to +50° C. thereby to form trimethylpyruvic acid amide. The derivative in (a) can be trimethylpyruvic acid amide or it may first be saponified to the free acid. The inorganic acid in (a) can be hydrochloric or hydrobromic acid in glacial acetic acid, or it can be concentrated sulphuric acid plus some chloride ion and followed by water. Trimethyl pyruvic acid amide is a new compound.

11 Claims, No Drawings

PREPARATION OF 4-AMINO-6-TERT.-BUTYL-3-ALKYLTHIO-1,2,4-TRIAZIN-5(4H)-ONES

The present invention relates to an unobvious process for the preparation of 4-amino-6-tert.-butyl-3-alkylthio-1,2,4-triazin-5(4H)-ones, which are known to be herbicidally active, and a novel intermediate therefor.

It is known from the literature that considerable difficulties are in principle associated with the preparation of α-ketocarboxylic acids and amides thereof by saponification of corresponding acyl cyanides, since it is virtually impossible completely to suppress splitting of the acyl cyanides into hydrocyanic acid and carboxylic acids containing one carbon atom less than the acyl cyanide employed (Angew. Chem. 68, page 430 (1956)).

It is already known, however, that pyruvic acid amide can be obtained in a good yield (up to 79%) by partial hydrolysis of pyruvic acid nitrile by treating the pyruvic acid nitrile, in ethereal solution, first with dry gaseous hydrogen chloride and then with water at about 0° C. and isolating the amide in the customary manner (see J. Amer. Chem. Soc. 73, page 5914 (1951)).

It has also been disclosed that certain C-substituted pyruvic acid amides, in particular amides of the general formula

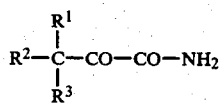

(I)

wherein
$R^1$ represents a hydrogen atom;
$R^2$ and $R^3$ are identical or different and represent an alkyl radical which is optionally substituted by halogen, and
$R^2$ also represents a hydrogen atom; or
$R^2$ and $R^3$ together complete a 3-membered to 8-membered cycloalkyl ring which is optionally substituted by alkyl or halogen, it being possible for $R^1$ also to represent an alkyl radical in this case.

can be obtained in high yields (up to 91%) in a corresponding manner when an appropriate acyl cyanide of the general formula

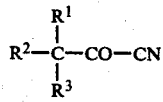

(II)

in which $R^1$, $R^2$ and $R^3$ have the abovementioned meaning, is reacted, in the presence of an inert organic solvent, such as, in particular, ether, first with gaseous hydrogen chloride and then with water at a temperature between −70° and +70° C., preferably between −40° and +20° C., and the end products are isolated in a manner which is in itself known (see German Published Specification DOS No. 2,708,184).

In the processes known from the state of the art, in contrast, it is not possible, as experiments performed by the applicants have shown, to prepare trimethylpyruvic acid amide of formula (III), which was hitherto unknown, in a significant yield in a corresponding manner from pivaloyl cyanide (a compound of formula (II) in which $R^1 = R^2 = R^3$ = methyl, or otherwise shown as formula (IV)).

It has also been disclosed that 4-amino-6-tert.-butyl-3-methylthio-1,2,4-triazin-5(4H)-one (VIII) is obtained when pivaloyl cyanide, of the formula

(IV), is reacted, in a first stage, with tert.-butanol or isobutylene in the presence of a strong acid, such as, in particular, sulphuric acid, if appropriate in the presence of an organic solvent, such as, in particular, glacial acetic acid, methylene chloride or a higher ether, at temperatures between −20° and +50° C. to give trimethylpyruvic acid N-tert.-butylamide, of the formula

(V), this compound, in a second stage and if appropriate after prior saponification to give free trimethylpyruvic acid, of the forumla

(VI), is subjected to a condensation reaction with thiocarbohydrazide ($H_2N-NH-CS-NH-NH_2$) to give 4-amino-6-tert.-butyl-3-mercapto-1,2,4-triazin-5(4H)-one, of the formula

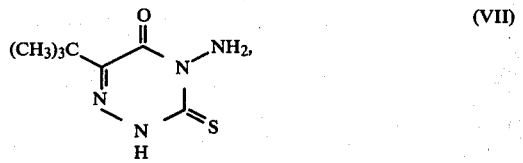

(VII)

and this compound is reacted, in a third stage, with a methylating agent, such as methyl iodide or bromide, in the customary manner to give 4-amino-6-tert.-butyl-3-methylthio-1,2,4-triazin-5(4H)-one, of the formula

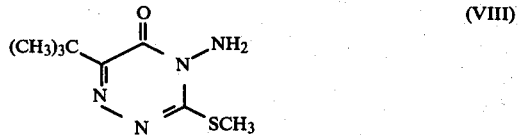

(VIII)

(see U.S. Pat. No. 4,175,188).

This process, the first stage of which proceeds under the conditions of the so-called Ritter reaction, has, however, the disadvantage that isobutylene or tert.-butanol must be employed as an auxiliary, and preferably in amounts greater than the stoichiometric amount.

The reaction of the α-keto-acid amide (V) with thiocarbohydrazide to give (VII) in the second process stage is already known in principle (see German Published Specification DOS No. 2,165,554). The reaction of the free α-keto-acid (VI) with thiocarbohydrazide to give (VII) has already been described (see, for example, German Published Specification No. 2,460,889. The third process stage has also already been described (see, for example, U.S. Pat. No. 3,752,808; German DOS No. 2,729,761 and U.S. Pat. No. 3,897,429; U.S. Pat. No. 4,035,364).

The present invention now provides a process for the preparation of 4-amino-6-tert.-butyl-3-alkylthio-1,2,4-triazin-5(4H)-ones of the formula

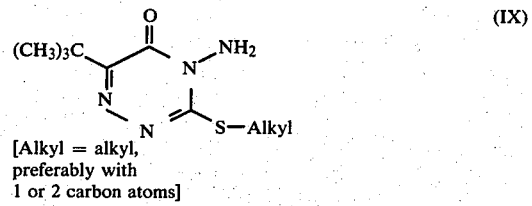

[Alkyl = alkyl, preferably with 1 or 2 carbon atoms]

in which pivaloyl cyanide is initially reacted, in a first stage, with a strong, anhydrous inorganic acid, if appropriate in the presence of a lower aliphatic carboxylic acid which is liquid under the reaction conditions, as a solvent, and if appropriate under pressure, and then, if appropriate, with water, in each case at a temperature between $-50°$ and $+50°$ C., and the trimethylpyruvic acid amide, of the formula $$(CH_3)_3C—CO—CO—NH_2 \qquad (III),$$

which is formed in step (1) and which was hitherto unknown, is reacted, in a second stage, either directly in the solution obtained or after intermediate isolation and if appropriate after prior saponification to give free trimethylpyruvic acid (VI), with thiocarbohydrazide ($H_2N—NH—CS—NH—NH_2$) in an aqueous solution containing a hydrogen halide acid, at a temperature from about 20° to 100° C. in a manner which is in itself known to give 4-amino-6-tert.-butyl-3-mercapto-1,2,4-triazin-5(4H)-one (VII), and this compound is alkylated in alkaline solution, in a third stage, by means of methyl iodide or methyl bromide or other alkylating agents (especially ethyl iodide or ethyl bromide) in a known manner.

According to the state of the art, it was not hitherto possible to hydrolyze pivaloyl cyanide to give trimethylpyruvic acid (VI) via trimethylpyruvic acid amide (III).

As is known, quite generally, the preparation of α-ketocarboxylic acids or amides thereof by saponification of corresponding acyl cyanides is associated with considerable difficulties, because, under the hydrolysis conditions, it is in practice impossible completely to suppress a splitting of the acyl cyanides into hydrocyanic acid and carboxylic acids containing 1 C atom less than the acyl cyanide employed (see Angew. Chem. 68, page 430 (1956)).

Under particular process conditions, however, it is possible to hydrolyze, in each case with good yields, pyruvic acid nitrile ($CH_3—CO—CN$) to give pyruvic acid amide ($CH_3—CO—CO—NH_2$), and certain C-substituted pyruvic acid nitriles of the general formula $R^1R^2R^3C—CO—CN$ (wherein $R^1$, $R^2$ and $R^3$ represent, with certain restrictions, hydrogen or optionally substituted alkyl or cycloalkyl radicals) to give the corresponding amides of the formula $R^1R^2R^3C—CO—CO—NH_2$ (see J. Amer. Chem. Soc. 73, page 5914 (1951) and U.S. Pat. No. 4,175,188). In this hydrolysis, the α-keto-carboxylic acid nitriles (=acyl cyanides) are first treated, in ethereal solution, with dry gaseous hydrogen chloride and then with water; the α-ketocarboxylic acid amides formed are isolated in the customary manner.

In contrast, experiments have shown it is not possible to hydrolyze trimethylpyruvic acid nitrile, that is to say pivaloyl cyanide (IV), to give trimethylpyruvic acid amide (III) in a significant yield by these processes known from the state of the art. In this respect, it is surprising that it is possible to obtain trimethylpyruvic acid amide (III) in a good yield under the conditions of the first stage of the process according to the invention, which makes the new and simplified synthesis route from pivaloyl cyanide to the herbicide metribuzin (VIII, Alkyl=$CH_3$) possible.

In particular, on the basis of the state of the art, it was not to be expected that stage 1 of the process according to the invention proceeds in good yields either without a solvent or in the presence of a lower aliphatic carboxylic acid as the solvent, since these organic acids are not to be regarded as inert, especially towards hydrogen halides, under the reaction conditions.

The process according to the invention avoids the above-mentioned disadvantages associated with the process which is most similar chemically for the preparation of the herbicidal active compound (VIII) (see U.S. Pat. No. 4,175,188); this means a considerable technical simplification.

Compared with other processes already known (see, for example German Published Specification DOS Nos. 2,003,144; 2,165,554; 2,460,889; 2,460,909; and 2,648,300) for the preparation of the active compound (VIII) from other pivalic acid derivatives or pinacolone, the process according to the invention also has the industrial advantage of marked simplification. Compared with the processes starting from pinacolone, the different raw material basis is to be seen as an additional advantage.

If glacial acetic acid is used as the solvent and hydrogen bromide is used as the inorganic acid in the first process stage, the amide intermediate product is reacted directly as such with thiocarbohydrazide in the second stage and methyl bromide is used as the alkylating agent in the third stage, the course of the reaction can again be represented, in summarized form, by the following equation:

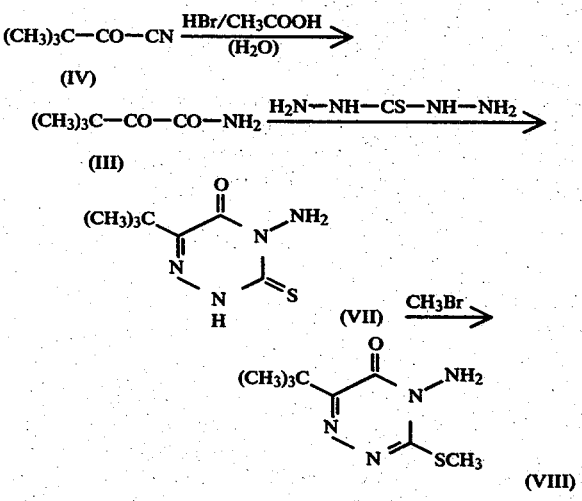

The pivaloyl cyanide (IV) used as the starting material is known and can be prepared, for example, by reacting pivaloyl chloride with copper (I) cyanide (see, for example, J. Amer. Chem. Soc. 72, page 2793 (1950)).

In detail, the following statements may also be made with regard to stage 1 of the process according to the invention:

The reaction temperatures can be varied within a substantial range in carrying out this process stage. In general, the reaction is carried out between −50° and +50° C., preferably at from −20° to +30° C., as indicated above.

The first process stage can be carried out not only under normal pressure, but also under increased pressure and preferably in the pressure range from 1 to 10 bars.

The first process stage is carried out with the aid of a strong inorganic acid. Such acids include, as preferences, the hydrogen halide acids, such as dry hydrogen chloride and hydrogen bromide, and concentrated sulphuric acid.

This process stage can be carried out in the absence or in the presence of a lower aliphatic carboxylic acid which is liquid under the reaction conditions, as a solvent. Possible solvents of this type are, in particular, carboxylic acids with 1 to 6 carbon atoms, for example anhydrous acetic acid, propionic acid or formic acid. Glacial acetic acid is particularly preferred.

A solvent is preferably used if a hydrogen halide is used as the inorganic acid, while the reaction is preferably carried out without a solvent if an inorganic oxyacid, such as, in particular, sulphuric acid, is used.

If an inorganic oxyacid is used, it may also be expedient to add chloride ions to the reaction mixture in the form of alkali metal chloride or ammonium chloride in catalytic amounts, preferably in amounts of 0.01 to 0.1 mole per mole of oxyacid. The addition of ammonium chloride is particularly suitable, for example, when sulphuric acid is used.

It is not absolutely necessary to add water to the reaction mixture for the formation of the amide (III) in the first process stage in those cases in which a carboxylic acid is used as the solvent and a hydrogen halide is used as the inorganic acid: in addition to a certain amount of carboxylic acid halide, the corresponding amount of water is formed by the action of the hydrogen halide on the carboxylic acid, and this amount can be sufficient to hydrolyze the pivaloyl cyanide employed or intermediate stages which may have been formed during the reaction. In such cases, the carboxylic acid employed functions not only as the solvent but also partly as a reactant (whereupon, needless to say, alternative reaction mechanisms are also conceivable). In any case, it is not necessary to employ a stoichiometric amount of water in this embodiment of the first process stage.

In carrying out the first stage of the process according to the invention, in general 1 to 10 moles of inorganic acid and 0 to 10 moles of water, preferably 1 to 8 moles of inorganic acid and 0 to 2.5 moles of water, are employed per mole of pivaloyl cyanide (IV).

The trimethylpyruvic acid amide (III) which is formed in this reaction stage can be intermediately isolated, if desired, in the customary manner.

The second stage of the process according to the invention is preferably carried out without prior intermediate isolation of the trimethylpyruvic acid amide (III) and without saponification thereof to give the free acid (VI).

The reaction is carried out in the presence of an aqueous solution containing a hydrogen halide acid, preferably hydrochloric acid.

The reaction temperatures can be varied within a substantial range in this process stage. In general, the reaction is carried out between 20° and 100° C., preferably between 50° and 90° C.

The starting substances are preferably employed in equimolar amounts in carrying out the second process stage. The intermediate product (VII) is isolated in the customary manner.

The third stage of the process according to the invention may be carried out in a known manner by reaction with an alkyl halide, such as methyl bromide or ethyl iodide, in the presence of a base, such as sodium hydroxide, in aqueous solution at a temperature between 0° and 50° C.

The 4-amino-6-tert.-butyl-3-alkylthio-1,2,4-triazin-5(4H)-ones of the formula (IX) which can be prepared according to the invention are distinguished, as is known, by a very good herbicidal activity (see, for example, German Patent Specification No. 1,795,784 or U.S. Pat. No. 3,671,523).

Alternatively the second stage can be carried out in two steps. In the first the trimethylpyruvic acid amide can be saponified in a manner which is in itself known, by acid or alkaline hydrolysis, to give the free trimethylpyruvic acid (3,3-dimethyl-2-oxo-butyric acid (VI)). The process according to the invention thus also makes possible, for the first time, direct hydrolysis of pivaloyl cyanide to give trimethylpyruvic acid, it not being necessary to isolate the amide intermediate product.

This means an advantageous simplification of the process compared with the process for the preparation of trimethylpyruvic acid from pivaloyl cyanide which is known from the state of the art (see U.S. Pat. No. 4,175,188), since the "round-about route" via the Ritter reaction and hence via the N-t-butylamide of trimethylpyruvic acid is avoided. The process according to the invention proceeds without the auxiliary t-butanol or isobutylene, which is required as an additional reagent in the case of the already known Ritter reaction.

Trimethylpyruvic acid of formula (VI) can be subjected to a condensation reaction with 1 to 1.5 moles of thiocarbohydrazide ($NH_2$—NH—CS—NH—$NH_2$) in aqueous solution containing a hydrogen halide acid, at a temperature between 20° and 100° C., to give 4-amino-6-tert.-butyl-3-mercapto-1,2,4-triazin-5(4H)-one of formula (VII).

Compared with trimethylpyruvic acid N-t-butylamide, which is already known, trimethylpyruvic acid amide of formula (III) has the advantage that it can be prepared more simply, as illustrated above, and that only ammonia in the form of ammonium salts is obtained as a by-product during further processing, whether by hydrolysis or by direct condensation with thiocarbohydrazide.

The active compound prepared according to the invention influences plant growth and can therefore be used as a defoliant, desiccant, agent for destroying broad-leaved plants, germination inhibitor and, especially, as a weedkiller. By "weeds" in the broadest sense there are meant plants growing in places where they are not desired.

Whether the compound prepared according to the invention acts as total herbicide or selective herbicide depends essentially on the amount used.

The active compound prepared according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound prepared according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Cryza, Zea, Triticum, Hordeum, Avena, Secale, Sorghum, Panicum, Saccharum, Ananas, Asparagus and Allium.

However, the use of the active compound is in no way restricted to these genera but also embraces other plants, in the same way.

Depending on the concentration, the compound can be used for the total combating of weeds, for example on industrial terrain and railway tracks and on paths and squares with or without trees. Equally, the compound can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

For combating weeds, the active compound can be used, as such or as a formulation, in admixture with other herbicides, it being possible to use finished formulations or tank mixing.

The active compound can be converted into the customary formulations, such as solutions, emulsions, suspensions, powders, foams, granules, natural and synthetic materials impregnated with active compound, and very fine capsules in polymeric substances.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound can be present in the formulations as a mixture with other active compounds, such as fungicides, insecticides, acaricides, nematicides, bird repallents, growth factors, plant nutrients and agents which improve soil structure.

The active compound can be used as such, in the form of its formulations or in the use forms prepared therefrom by further dilution, such as ready-to-use solutions, suspensions, emulsions, powders and granules. They may be used in the customary manner, for example by watering, spraying, atomizing or scattering.

The active compound prepared according to the invention can be applied either before or after emergence of the plants. It can also be incorporated into the soil before sowing.

The amount of active compound used can vary within a substantial range. It depends essentially on the nature of the desired effect. In general, the amounts used are between 0.05 and 10 kg of active compound per hectare, preferably between 0.1 and 5 kg/ha.

The present invention also provides a herbicidal composition containing as active ingredient the compound prepared according to the present invention in admixtue with a solid diluent or carrier or in admixture with a liquid diluent or carrier containing a surface-active agent.

The present invention also provides a method of combating weeds which comprises applying to the weeds, or to a habitat thereof, the compound prepared according to the present invention alone or in the form of a composition containing as active ingredient the compound in admixture with a diluent or carrier.

The present invention further provides crops protected from damage by weeds by being grown in areas in which immediately prior to and/or during the time of the growing the compound prepared according to the present invention was applied alone or in admixture with a diluent or carrier.

The preparative examples which follow are intended to illustrate the process according to the invention in more detail.

PREPARATIVE EXAMPLES (A) Preparation of trimethylpyruvic acid amide

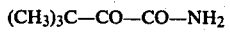
(III)

EXAMPLE 1

111.0 g (1 mole) of pivaloyl cyanide were added dropwise to 800 g of a 36% strength solution of hydrogen bromide in glacial acetic acid at room temperature, while stirring. When the addition had ended, the mixture was subsequently stirred at room temperature for 3 hours. 9 ml (0.5 mole) of water were then added dropwise at 20° to 25° C. and the mixture was subsequently stirred at room temperature for 1 hour. The reaction solution was then poured into an excess of saturated sodium bicarbonate solution. It was extracted three times with 200 ml of methylene chloride each time. The combined organic phases were washed with 200 ml of water, dried over sodium sulphate and concentrated by distilling off the solvent in vacuo. After some time, the oil which remained crystallized completely. The recrystallization from petroleum ether gave 113.5 g (88% of theory) of trimethylpyruvic acid amide of melting point 69° to 70° C.

EXAMPLE 2

Hydrogen chloride was passed into a mixture of 60 g (1 mole) of glacial acetic acid and 111.0 g (1 mole) of pivaloyl cyanide at 20° to 25° C. and under 8 bars for 5 hours. The reaction mixture was then let down and poured onto an excess of a saturated sodium bicarbonate solution. The mixture was extracted three times with 200 ml of methylene chloride each time. The combined organic phases were washed with 200 ml of water, dried over sodium sulphate and concentrated by distilling off the solvent in vacuo. The residue which remained crystallized after a short time. Recrystallization from petroleum ether gave 97 g (75.2% of theory) of trimethylpyruvic acid amide of melting point 68° to 69° C.

EXAMPLE 3

55.5 g (0.5 mole) of pivaloyl cyanide and 2 g of ammonium chloride were introduced into a 500 ml three-necked flask. The mixture was cooled to −5° to 0° C. and 100 ml of concentrated sulphuric acid was added dropwise at this temperature. 18 ml (1 mole) of water were then added dropwise, also at −5° to 0° C. The reaction mixture was subsequently stirred at −5° to 0° C. for 12 hours and was then poured onto a solution of 350 g of sodium carbonate in 600 ml of water. It was extracted twice with 300 ml of methylene chloride each time. The combined organic phases were washed with 300 ml of water, dried over sodium sulphate and concentrated by distilling off the solvent in vacuo. Recrystallization from petroleum ether gave 66 g (51.2% of theory) of trimethylpyruvic acid amide of melting point 67° to 69° C.

(B) Preparation of 4-amino-6-tert.-butyl-3-methylthio-1,2,4-triazin-5(4H)-one (VIII)

EXAMPLE 4

1st and 2nd stage 111.0 g (1 mole) of pivaloyl cyanide were added dropwise to 800 g of a solution of hydrogen bromide in glacial acetic acid (36% strength) at room temperature. When the addition had ended, the mixture was subsequently stirred at room temperature for three hours. 9 ml (0.5 mole) of water were then added dropwise at 20° to 25° C. and the mixture was subsequently stirred at room temperature for one hour. Thereafter, the glacial acetic acid and the excess hydrogen bromide were stripped off in vacuo and the trimethylpyruvic acid amide obtained was introduced into a mixture of 107.6 g of thiocarbohydrazide, 420 g of water and 140.6 g of concentrated hydrochloric acid. This reaction mixture was subsequently stirred at 90° C. for 1.5 hours and at room temperature for 12 hours. It was then cooled to 0° C. and the crystals precipitated were filtered off, washed with 200 ml of water and dried at 100° C. in vacuo. 168.6 g (84.3% of theory) of 4-amino-6-tert.-butyl-3-mercapto-1,2,4-triazin-5(4H)-one (VII) of melting point 205° to 209° C. were obtained.

3rd stage 168.6 g (0.84 mol) of 4-amino-6-tert.-butyl-3-mercapto-1,2,4-triazin-5(4H)-one were introduced into a mixture of 820 g of 45% strength sodium hydroxide solution and 550 g of water, while stirring. When the product had dissolved completely, 140 g of methyl iodide were added in a manner such that the internal temperature did not exceed 30° C. When the addition had ended, the reaction solution was stirred for a further two hours at room temperature. Thereafter, the solid formed was filtered off, washed with 1,000 ml of water and dried at 60° C. in a vacuum drying cabinet. 146 g (81% of theory) of 4-amino-6-tert.-butyl-3-methylthio-1,2,4-triazin-5(4H)-one (VIII) of melting point 123°–125° C. were obtained.

EXAMPLE 5

Hydrogen chloride gas was passed into a mixture of 222 g (2 mol) of pivaloyl cyanide and 120 g (2 mol) of glacial acetic acid under 8 bars and at 20° to 25° C. for four hours. Thereafter, the mixture was let down and excess glacial acetic acid was stripped off in vacuo. The product was then added to a mixture of 212 g (2 mol) of thiocarbohydrazide, 840 g of water and 280 g of concentrated hydrochloric acid. When the addition had ended, the reaction mixture was warmed to 90° C. for 1.5 hours and then subsequently stirred at room temperature overnight. The mixture was then cooled to 0° C. and the solid obtained was filtered off, washed with 400 ml of cold water and dried at 40° C. in vacuo. 314.4 g (78.6% of theory) of 4-amino-6-tert.-butyl-3-mercapto-1,2,4-triazin-5(4H)-one (VII) of melting point 205°–209° C. were obtained.

The methylation of (VII) to give (VIII) was carried out according to Example 4.

EXAMPLE 6

200 ml of concentrated sulphuric acid and then 72 g of water were added dropwise to 111 g (1 mol) of pivaloyl cyanide at 20° to 25° C. The reaction mixture was subsequently stirred at 20° to 25° C. for 20 hours and was added to a solution of 106 g (1 mol) of thiocarbohydrazide in 500 ml of water and 150 ml of concentrated hydrochloric acid at the above temperature. The mixture was subsequently stirred at 80° to 90° C. for 2 hours, cooled to 5° to 10° C. and filtered. The solid residue was recrystallized from methanol. 130 g (65% of theory) of 4-amino-6-tert.-butyl-3-mercapto-1,2,4-triazin-5(4H)-one (VII) of melting point 216° C. were obtained.

The methylation of (VII) to give (VIII) was carried out according to Example 4.

It will be appreciated that the instant specification and examples are set forth by way of illustration and not limitation, and that various modifications and changes may be made without departing from the spirit and scope of the present invention.

What is claimed is:

1. In the preparation of 4-amino-6-tert.-butyl-3-alkylthio-1,2,4-triazin-5(4H)-one of the formula

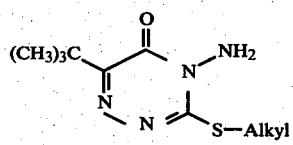

wherein (a) pivaloyl cyanide of the formula

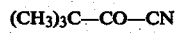

is converted to derivative of trimethylpyruvic acid. (b) the derivative is condensed with thiocarbohydrazide of the formula

to form 4-amino-6-tert.-butyl-3-mercapto-1,2,4-triazin-5(4H)-one, and (c) that is alkylated to form the indicated end products, the improvement which comprises effecting (a) by reacting the pivaloyl cyanide with a strong anhydrous inorganic acid at about −50° to +50° C. thereby to form trimethylpyruvic acid amide and condensing said amide in (b) with the thiocarbohydrazide.

2. A process according to claim 1, wherein (a) is carried out at a temperature between about −20° and +30° C.

3. A process according to claim 1, wherein (a) is carried out in the pressure range from about 1 to 10 bars.

4. A process according to claim 1, wherein the amide formed in (a) is saponified to trimethylpyruvic acid which is condensed with the thiocarbohydrazide.

5. A process according to claim 1, wherein the trimethylpyruvic acide amide without isolation is reacted directly with the thiocarbohydrazide.

6. A process according to claim 1, wherein the reaction with the inorganic acid is effected in the presence of a lower aliphatic carboxylic acid which is liquid under the reaction conditions.

7. A process according to claim 6, wherein the inorganic acid in (a) is hydrogen chloride or hydrogen bromide, and it is present in 1 to 10 times the molar amount of the pivaloyl cyanide.

8. A process according to claim 7, wherein the lower aliphatic carboxylic acid is glacial acetic acid.

9. A process according to claim 1, wherein the inorganic acid is an inorganic oxyacid and water is thereafter added.

10. A process according to claim 9, wherein about 1 to 8 moles of concentrated sulphuric acid as the inorganic oxyacid and 0 to 2.5 moles of water are employed per mole of pivaloyl cyanide, and the reaction is effected in the absence of a solvent.

11. A process according to claim 9, wherein about 0.01 to 0.1 mole of chloride ion is present per mole of the oxyacid.

* * * * *

UNITED STATES PATENT AND TRADEMARK OFFICE
CERTIFICATE OF CORRECTION

PATENT NO. : 4,309,538
DATED : Jan. 5, 1982
INVENTOR(S) : Thomas Schmidt et al

It is certified that error appears in the above-identified patent and that said Letters Patent are hereby corrected as shown below:

Title Page Priority    Delete "Jan. 31, 1981" and insert --Jan. 31, 1980--.

Signed and Sealed this

Twenty-fifth Day of May 1982

[SEAL]

Attest:

*Attesting Officer*

GERALD J. MOSSINGHOFF

*Commissioner of Patents and Trademarks*